(12) United States Patent
Terahara et al.

(10) Patent No.: US 8,696,638 B2
(45) Date of Patent: Apr. 15, 2014

(54) MICRONEEDLE ARRAY

(75) Inventors: Takaaki Terahara, Tsukuba (JP); Seiji Tokumoto, Tsukuba (JP); Akira Tamura, Tokyo (JP); Yumiko Yamada, Tokyo (JP)

(73) Assignees: Hisamitsu Pharmaceutical Co., Inc., Tosu-shi, Saga (JP); Toppan Printing Co., Ltd., Taito-Ku, Tokyo (JP)

(*) Notice: Subject to any disclaimer, the term of this patent is extended or adjusted under 35 U.S.C. 154(b) by 0 days.

(21) Appl. No.: 13/386,105

(22) PCT Filed: Jul. 15, 2010

(86) PCT No.: PCT/JP2010/062008
§ 371 (c)(1),
(2), (4) Date: Feb. 16, 2012

(87) PCT Pub. No.: WO2011/010605
PCT Pub. Date: Jan. 27, 2011

(65) Prior Publication Data
US 2012/0136312 A1    May 31, 2012

(30) Foreign Application Priority Data

Jul. 23, 2009  (JP) .............................. P2009-172525

(51) Int. Cl.
*A61M 5/00*    (2006.01)
*A61N 1/30*    (2006.01)

(52) U.S. Cl.
USPC .............................. 604/173; 604/187; 604/21

(58) Field of Classification Search
CPC ...................... A61M 25/0012; A61M 25/0014; A61M 2025/0006; A61M 25/0015; A61M 2037/0023; A61M 3037/0038; A61M 2037/0053; A61M 5/3129; A61M 5/24; A61M 5/31511; A61M 2005/3139; A61M 5/3135
USPC ............................................. 604/173, 21, 187
See application file for complete search history.

(56) References Cited

U.S. PATENT DOCUMENTS

| 7,914,813 B2 | 3/2011 | Adachi et al. |
| 2004/0049150 A1 | 3/2004 | Dalton et al. |

(Continued)

FOREIGN PATENT DOCUMENTS

| JP | 11-286439 A | 10/1999 |
| JP | 2001-506904 A | 5/2001 |

(Continued)

OTHER PUBLICATIONS

Harvinder S. Gill and Mark R. Prausnitz, "Coating Formulations for Microneedles", Pharmaceutical Research, vol. 24, No. 7, Jul. 2007, pp. 1369-1380.

(Continued)

*Primary Examiner* — Aarti Bhatia Berdichevsky
*Assistant Examiner* — Niyati D Shah
(74) *Attorney, Agent, or Firm* — Nath, Goldberg & Meyer; Sheldon M. McGee (57) ABSTRACT

Relations between crystallinity and performance of a biodegradable resin, between weight-average molecular weight and strength thereof, and between weight-average molecular weight and performance thereof were clarified. As a result thereof, when a microneedle array was provided with microneedles containing noncrystalline polylactic acid which had a weight-average molecular weight of 40,000 to 100,000, it was possible to obtain a microneedle array which could maintain its functional performance.

10 Claims, 4 Drawing Sheets

(56) References Cited

U.S. PATENT DOCUMENTS

| | | |
|---|---|---|
| 2006/0127465 A1* | 6/2006 | Maenosono et al. .......... 424/449 |
| 2006/0163215 A1 | 7/2006 | Maenosono et al. |
| 2007/0250018 A1 | 10/2007 | Adachi et al. |
| 2008/0312610 A1 | 12/2008 | Binks et al. |
| 2009/0030365 A1 | 1/2009 | Tokumoto et al. |
| 2009/0099502 A1 | 4/2009 | Tokumoto et al. |

FOREIGN PATENT DOCUMENTS

| | | |
|---|---|---|
| JP | 2004-504120 A | 2/2004 |
| JP | 2005-21677 A | 1/2005 |
| JP | 2005-21678 A | 1/2005 |
| JP | 2006-341089 A | 12/2006 |
| JP | 2007037626 A | 2/2007 |
| JP | 2007-260351 A | 10/2007 |
| JP | 2008-212588 A | 9/2008 |
| JP | 2009-502261 A | 1/2009 |
| JP | 2009-45766 A | 3/2009 |
| JP | 2009-72271 A | 4/2009 |
| WO | 9828037 A1 | 7/1998 |
| WO | 2005044366 A2 | 5/2005 |
| WO | 2005069758 A2 | 8/2005 |
| WO | 2006/075689 A1 | 7/2006 |
| WO | 2006/075716 A1 | 7/2006 |
| WO | 2006121110 A1 | 11/2006 |
| WO | 2008/096732 A1 | 8/2008 |
| WO | 2008/139648 A1 | 11/2008 |
| WO | 2009/051147 A1 | 4/2009 |

OTHER PUBLICATIONS

Chisato Yoshimura, et al., "Polylactic Acid-Sei Microneedle Array no Kino Hyoka", Abstract of Annual Meeting of Pharmaceutical Society of Japan, No. 124th, No. 4, III-173, 2004, p. 68.

Chisato Yoshimura, et al. "Polylactic Acid-sei Microneedle Array no Kino Hyoka", Abstract of Annual Meeting of Pharmaceutical Society of Japan, 2004, No. 124th, No. 4, III-173, p. 68.

International Search Report issued for corresponding International PCT Application No. PCT/JP2010/062008, mailed Aug. 10, 2010, two pages.

International Preliminary Examination Report for PCT/JP2010/062008: 10 pages; mailed on Feb. 16, 2012.

Tian Yi, et al., "Structure, property and prospect of polylactic acid", Petrochemical Technology & Application, vol. 24, No. 3; May 31, 2006; pp. 233-237. Separate English partial translation.

Official Action issued in CN Patent Application No. 201080025511.9 on Nov. 13, 2012; six pages.

* cited by examiner

MICRONEEDLE ARRAY

This is a National Phase Application filed under 35 U.S.C. §371 as a national stage of PCT/JP2010/062008, filed on Jul. 15, 2010, an application claiming the benefit under 35 U.S.C. §119 of Japanese Application No. P2009-172525, filed on Jul. 23, 2009, the content of each of which is hereby incorporated by reference in their entirety.

TECHNICAL FIELD

The present invention relates to a microneedle array including one or more microneedles capable of piercing skin on a base for administration of drugs to a living body, sucking extraction of blood from a living body, or the like.

BACKGROUND ART

Conventionally, a microneedle array has been known as a device for improving transdermal absorption of drugs. Microneedles provided on the microneedle array are intended to pierce the stratum corneum, which is an outermost skin layer, and various sizes and shapes thereof have been proposed. A microneedle device is expected as a non-invasive administration method (for example, see Patent Literature 1).

Further, various methods have been proposed in regard to a method of applying drugs by use of a microneedle array. Coating the surface of microneedles with drugs, forming a groove or a hollow part in microneedles through which drugs or body components are allowed to penetrate, mixing drugs into microneedles themselves, and the like are known (Patent Literature 2).

Patent Literature 3 states that in a drug transdermal pad base, in a case where fine needles provided on a skin-side surface thereof are made from a biodegradable resin, even if a tip of a fine needle is chipped and remains in skin, the fine needle made from the biodegradable resin is degraded within a living body, thereby causing little adverse effect on the living body, and that as the biodegradable resin, polylactic acid, polyethylene succinate, polybutylene succinate adipate, polybutylene succinate carbonate, polycaprolactone, polyester amide, polyester carbonate, polyvinyl alcohol, polyhydroxy butylate, maltotriose, cellulose, cellulose acetate, collagen, and mixtures thereof are recommended, and polylactic acid or a copolymer of lactic acid and glycolic acid is particularly preferable.

Further, Patent Literature 3 states that in the case of polylactic acid, when its molecular weight is 100,000 to 500,000, an amount thereof deposited to the aforementioned metal thin wire is suitable in view of production, a pulling-out property of the metal thin wire after hardening of the resin is good, and the quality of a finished film (a tubular object) is also excellent. However, Patent Literature 3 does not describe anything about weight-average molecular weight and strength.

Patent Literature 4 discloses that in a drug release system which can select and perform any of controlled biphasic release, sustained release, and delayed release, pulverized polylactic acid having a weight-average molecular weight of 3000 to 40,000 is used, but it does not describe anything about a microneedle array capable of piercing skin at all.

CITATION LIST

Patent Literature

Patent Literature 1: National Publication of International Patent Application No. 2001-506904

Patent Literature 2: National Publication of International Patent Application No. 2004-504120

Patent Literature 3: Japanese Patent Application Laid-Open No. 2005-021678

Patent Literature 4: Japanese Patent Application Laid-Open No. 11-286439

SUMMARY OF INVENTION

Technical Problem

When a microneedle array is produced from a biodegradable resin, a step of deforming the biodegradable resin into a desired shape by heating it to be softened, and a sterilization operation or the like by an electron-beam irradiation treatment, etc. are required. However, this causes a problem: due to the strength of the microneedle array (especially, a microneedle portion) during such steps, the microneedles which are essentially supposed to pierce skin cannot perform its function, or the base of the microneedle array is broken at the time of use and cannot perform its function, or there is a difficulty in manufacturing.

In view of this, it is an object of the present invention to provide a microneedle array which maintains functional performance of a microneedle array and which can easily be produced.

Solution to Problem

To achieve the above object, relations between crystallinity and performance of a biodegradable resin, between weight-average molecular weight and strength thereof and between weight-average molecular weight and performance thereof have been clarified. As a result thereof, it has been found that microneedles containing noncrystalline polylactic acid are excellent in maintaining their strength and have excellent performance, and further that the weight-average molecular weight thereof and the strength are well correlated with each other, but unexpectedly, the weight-average molecular weight and the performance are not necessarily correlated with each other. Based on this knowledge, the provision of a microneedle array that maintains functional performance has been enabled.

That is, the present invention is a microneedle array including microneedles containing noncrystalline polylactic acid.

Further, it is preferable that crystallinity of the polylactic acid be 38% or less.

Further, it is preferable that the microneedles be transparent or translucent.

Further, it is preferable that the polylactic acid have a weight-average molecular weight of 40,000 to 100,000.

Further, in this microneedle array, it is preferable that the polylactic acid be poly-L-lactic acid.

Further, it is preferable that this microneedle array be sterilized by electron-beam or gamma-ray irradiation.

Advantageous Effects of Invention

According to the present invention, it is possible to provide a microneedle array which maintains functional performance and which is easily produced.

DESCRIPTION OF EMBODIMENTS

Hereinbelow, an embodiment of a needle array according to the present invention will be described with reference to drawings.

Figure 1:
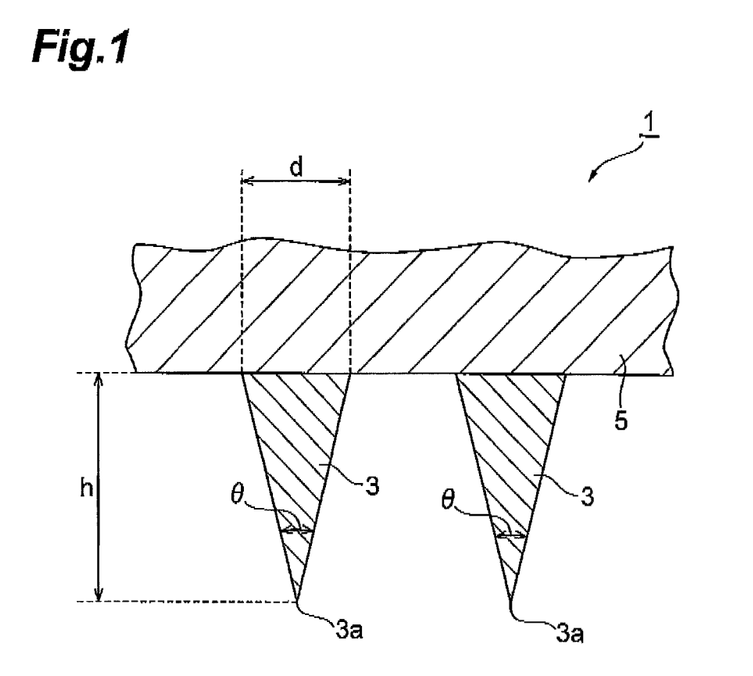
FIG. 1 is an enlarged cross-sectional view schematically showing a microneedle array according to the present invention.

As shown in FIG. 1, a microneedle array 1 is constituted by microneedles (needles) 3 for piercing skin or a mucous membrane and a microneedle base 5 which supports them, and thus, a plurality of microneedles 3 are arrayed on the microneedle base 5. The microneedle 3 has a minute structure, and a height (length) h of the microneedle 3 is preferably 50 μm to 700 μm. Here, the reason why the length h of the microneedle 3 is set to 50 μm or more is to surely perform transdermal administration of physiologically active ingredients and the reason why the length h thereof is set to 700 μm or less is to avoid the contact of a nervous system with the microneedle 3, thereby making it surely possible to reduce possibilities of pain, and to surely avoid possibilities of bleeding at the same time. Further, when the length h is 700 μm or less, it is possible to efficiently administer an amount of physiologically active ingredients penetrating the skin.

At this point, the microneedle 3 refers to a projecting structure including, in a broad sense, a needle shape or a structure containing a needle shape, and when the microneedle 3 has a conical-shaped structure, a diameter d of a basal surface thereof is generally about 50 to 200 μm. Further, the microneedle 3 is not limited to a structure having a needle shape, in a narrow sense, with a tapered tip but also includes a structure without a tapered tip, microscopically. In consideration of cases where the microneedle 3 is broken on skin, the microneedle 3 is produced from polylactic acid, which is a biodegradable resin. In some cases, physiologically active ingredients may be mixed in the resin so that the physiologically active ingredients can be released in a body at the same time as the microneedle 3 is dissolved in the body.

A tip 3a of the microneedle 3 may be microscopically flat, round or uneven, but in consideration of piercing skin or a mucous membrane, it is preferable that an area (assumed area) thereof when it is assumed that the tip 3a is flat be 1600 μm² or less, more preferably 400 μm² or less. Note that an assumed area when the tip 3a is microscopically round or uneven indicates a cross-sectional area of the tip 3a cut on a plane which perpendicularly intersects a longitudinal direction of the microneedle 3.

Further, in a case where the microneedle 3 has a conical (tapered) structure, when a tip angle (an angle of inclination) θ is 15 degrees or less, the microneedle 3 is easy to be broken, but when the tip angle θ is 25 degrees or more, it is difficult for the microneedle 3 to pierce skin or a mucous membrane. In view of this, the tip angle θ is preferably 15 degrees to 25 degrees.

The polylactic acid contained in the microneedle 3 according to the present embodiment is noncrystalline.

The microneedle 3 containing noncrystalline polylactic acid has an excellent mechanic characteristic, and is hard to be broken although it is deformed by pressing. On the other hand, a microneedle containing high-crystallinity polylactic acid is easy to be broken when given power is applied thereto. Therefore, the noncrystalline microneedle array 1 makes it difficult for a broken piece of the microneedle array 1 to remain in a body when it is used. Further, the noncrystalline polylactic acid causes no strength degradation of the microneedles 3 over time, and allows good storage stability. Further, in the case of a high-crystallinity microneedle array, for example, the following problem may occur: when physiologically active ingredients such as a drug are applied to the microneedle array, the physiologically active ingredients adsorb onto the microneedle array and are difficult to release in a body.

In short, when the microneedle array 1 includes microneedles 3 containing noncrystalline polylactic acid, it is possible to realize the microneedle array 1 which has an excellent mechanic characteristic and which has good storage stability. Further, as described later, when the microneedles 3 are formed by use of high-purity polylactic acid, it is easy to visually evaluate whether a microneedle array is the microneedle array 1 containing noncrystalline polylactic acid or not, that is, whether it is the microneedle array 1 having good storage stability or not, which is advantageous from the viewpoint of quality control as well.

Here, the noncrystalline polylactic acid is polylactic acid having a crystallinity of 38% or less. Note that the crystallinity is preferable to be low as much as possible, but the lower limit thereof is a crystallinity of 2% or more. It is difficult to set the crystallinity to 2% or less in view of the production of microneedles. The crystallinity of polylactic acid can be found by DSC (differential scanning calorimetry). After sampling a microneedle, a crystallization enthalpy and a fusion enthalpy are found in a temperature rising mode respectively from the heat capacity by an exothermic peak at crystallization temperature (around 100° C.) and from the heat capacity by an endothermic peak at a melting point (around 180° C.), and then the crystallinity can be found by using the fact that a crystallinity (xc) is given in accordance with xc (%)=100·(ΔHm+ΔHc)/93 where a fusion enthalpy of 93 J/g, which is of a PLLA crystal with an infinite lamella size, is used.

In order to form microneedles containing noncrystalline polylactic acid, the crystallinity of polylactic acid is controlled by the following method, and thus microneedles containing noncrystalline polylactic acid can be formed. A microneedle array can be obtained by providing a duplication plate in which the projection and recess shape of the microneedle array is reversed; filling minute-pattern portions of the duplication plate with polylactic acid which is melted by heating; and cooling down and peeling off the polylactic acid. At this time, the crystallinity can be controlled according to cooling velocity of the polylactic acid thus melted by heating, or time for heating the polylactic acid at about the crystallization temperature after cooling. More specifically, by performing rapid cooling while accelerating the cooling velocity of the polylactic acid thus melted by heating, microneedles containing noncrystalline polylactic acid having a low crystallinity can be formed. On the other hand, when the cooling velocity of the polylactic acid thus melt by heating is slowed to slowly cool it down, or when the polylactic acid is warmed and maintained at about the crystallization temperature after cooling, the crystallinity of the polylactic acid contained in the microneedles increases.

As the polylactic acid used for the microneedles, generally, polylactic acid in which the purity of polylactic acid is 95.0 wt % or more, the amount of residual monomer is 5 wt % or less, and the amount of residual Sn is 200 ppm or less is used. Especially, as the polylactic acid used for the microneedles, it is preferable to use high-purity polylactic acid in which the purity of polylactic acid is 98.7 wt % or more, and the amount of monomer remaining is 2 wt % or less, and the amount of residual Sn is 50 ppm or less. When the amount of monomer remaining and the amount of residual Sn in the polylactic acid increases, deterioration by molding/sterilization processes and strength deterioration over time are easy to occur, and further there is a concern about adverse effects to a living body. The high-purity and noncrystalline polylactic acid is excellent in transparency.

When the microneedles are produced by use of the high-purity polylactic acid in which the purity of polylactic acid is 98.7 wt % or more, the amount of monomer remaining is 2 wt % or less, and the amount of residual Sn is 50 ppm or less, whether polylactic acid is noncrystalline or not can be determined by a white-turbid state of the microneedle array. When the polylactic acid of the microneedles is noncrystalline, the microneedle array is transparent or translucent. Here, to be "transparent or translucent" means that a brightness index value $L^*$ is 60 or less when a color difference to a color-difference reference color (black) is measured by use of a colorimeter (CR-200, a product made by Minolta Co., Ltd) by taking the brightness index value $L^*$ as an index. Thus, it can be determined that a transparent or translucent microneedle having a brightness index value $L^*$ of 60 or less is a microneedle containing noncrystalline polylactic acid.

Further, examples of the polylactic acid include polylactic acid homopolymers such as poly-L-lactic acid and poly-D-lactic acid, a polyL/D-lactic acid copolymer, and a mixture thereof, but any of these may be used. Note that, in general, when respective homopolymers of poly-L-lactic acid and poly-D-lactic acid are used to form microneedles, and a crystallization process is performed, the microneedles have a high crystallinity of polylactic acid. On the other hand, when microneedles are formed using a polyL/D-lactic acid copolymer, the microneedles can be noncrystalline microneedles having a low crystallinity of polylactic acid. In the microneedle array 1 according to the present embodiment, it is preferable to produce a noncrystalline microneedle array 1 by use of poly-L-lactic acid from the viewpoint of safety. Further, additives such as a plasticizer, an anti-blocking agent, a lubricant, an antistatic agent, and a heat stabilizer can be added to the polylactic acid as appropriate.

The polylactic acid resin tends to have higher strength as its weight-average molecular weight is larger. It is necessary for the weight-average molecular weight of the polylactic acid of the microneedles 3 according to the present embodiment to be 40,000 or more from the viewpoint of strength. A weight-average molecular weight of less than 40,000 is not preferable because the strength of the microneedles 3 is low and piercing characteristics to skin decrease, and further because a yield of the microneedles 3 at the time of the production thereof tends to decrease.

Further, the weight-average molecular weight of the polylactic acid of the microneedles 3 according to the present embodiment is 100,000 or less. The weight-average molecular weight of 100,000 or less is preferable because piercing characteristics of the microneedles 3 to skin are sufficient, and further, even if a needle tip remains in a body, it is immediately degraded in the body. On the other hand, for producing microneedles containing polylactic acid having a weight-average molecular weight of more than 100,000, the melt viscosity of the polylactic acid is too high, and processing to the microneedles 3 becomes difficult, thereby decreasing the yield.

In the microneedle array 1 according to the present embodiment, it is preferable to perform a sterilization process from the viewpoint of safety. A sterilization process can be performed by a well-known method that is generally performed, but it is preferable for sterilization of the microneedle array 1 to be performed by electron-beam irradiation or gamma-ray irradiation. Measurement of an electron-beam irradiation dose is performed on the top or bottom of an irradiation sample, or on a supporting material (e.g., a "cardboard"), and thus it is possible to check that the sample is irradiated with a predetermined irradiation dose (under an irradiation environment with a temperature of 15° C. and a humidity of 15%). On the other hand, in the case of the gamma-ray irradiation, an irradiation sample can be irradiated with cobalt-60 gamma rays according to a designated irradiation dose of 5 to 100 kGy. As the sterilization process, not only sterilization by electron-beam irradiation or gamma-ray irradiation but also heat sterilization and EOG (ethylene oxide gas) sterilization can be used, but there are such concerns that the heat sterilization may cause polylactic acid to degrade, and that the EOG sterilization may causes remaining of a drug. The sterilization by electron-beam irradiation or gamma-ray irradiation does not cause such concerns, and therefore is used preferably.

In regard to the polylactic acid which constitutes the microneedle array 1 according to the present embodiment, it was found that its weight-average molecular weight decreases during the production and the sterilization process. Thus, in order to optimize the strength and performance of the microneedle array 1, it is necessary for the weight-average molecular weight of the polylactic acid after the production of the microneedle array 1 to be 40,000 to 100,000.

For example, although the weight-average molecular weight decreases to around 65 to 99% of an original weight-average molecular weight thereof due to electron-beam irradiation, in order to keep the strength even after the electron-beam irradiation, it is necessary for the weight-average molecular weight to be 40,000 or more. Thus, before the electron-beam irradiation, it is necessary for the weight-average molecular weight to be at least 40,000 or more.

More preferably, it is necessary for the weight-average molecular weight to be 50,000 or more in terms of strength after the electron-beam irradiation. In view of this, before the electron-beam irradiation, it is necessary for the weight-average molecular weight to be at least 50,000 or more.

Thus, if the weight-average molecular weight after the electron-beam irradiation is 40,000 or more, the microneedle 3 can be used without losing its performance. However, preferably, it is necessary for the weight-average molecular weight after the electron-beam irradiation to be 50,000 or more.

Note that in consideration of a preferable range of the weight-average molecular weight of the polylactic acid constituting the microneedle array 1, a molecular weight distribution (Mw/Mn) obtained by dividing a weight-average molecular weight (Mw) by a number average molecular weight (Mn) is preferably 2.75 or less, and more preferably 1.43 to 1.72 (see Table 1 and Table 6).

The microneedle base 5 is a foundation to support the microneedles 3. A configuration thereof is not limited, and may be, for example, a base having holes penetrating therethrough, which allows for administration of physiologically active ingredients from the back of the base. Examples of a material of the microneedles 3 or the microneedle base 5 include silicon, silicon dioxide, ceramics, metals (such as stainless steel, titanium, nickel, molybdenum, chromium, and cobalt), and synthetic or natural resin materials, but in consideration of the antigenicity of the microneedles 3 and the unit price of the material, biodegradable polymers such as polylactic acid, polyglycolide, polylactic acid-co-polyglycolide, pullulan, caprolactone, polyurethane, and polyanhydride, and synthetic or natural resin materials such as polycarbonate, polymethacrylic acid, ethylenevinyl acetate, polytetrafluoroethylene, and polyoxymethylene, which are non-biodegradable polymers, are particularly preferable. Further, the base may be integrated with the microneedles 3 in some cases, and, in those cases, the base is made from the same material as the aforementioned resin material of the microneedles 3.

The area of the microneedle base 5 is 0.5 $cm^2$ to 10 $cm^2$, preferably 1 $cm^2$ to 5 $cm^2$, and more preferably 1 $cm^2$ to 3 $cm^2$. Note that several microneedle bases 5 can be connected in combination to have a more favorite size.

As to the density of the microneedles (needles) 3, rows of the microneedles 3 are typically spaced apart so that a density of approximately 1 to 10 needles per millimeter (mm) is provided. Generally, adjacent rows are spaced apart from each other by a distance substantially equal to the space between the needles in a row, and the needle density is 100 to 10000 needles per 1 $cm^2$. When there is a needle density of 100 needles or more, the needles can efficiently pierce skin. Meanwhile, a needle density of more than 10000 needles makes it difficult to give the microneedles 3 strength capable of piercing skin. The density of the microneedles (needles) 3 is preferably 200 to 5000 needles, more preferably 300 to 2000 needles, and most preferably 400 to 1600 needles per $cm^2$. When the density exceeds 1600 needles, production of a microneedle array original plate, for example, by precision machining such as a dry etching process, laser processing or dicing processing tends to be difficult.

Examples of a production method of the microneedle array original plate include a wet etching process or a dry etching process using a silicon base, precision machining using metals or resins (such as an electric discharge method, laser processing, dicing processing, a hot embossing process, and injection mold processing), and machinery cutting. By these processing methods, microneedles, which are needles in the microneedle array original plate, and a microneedle base for supporting them are molded into an integrated unit. Examples of a method for hollowing a microneedle, which is a needle, includes a method in which, following the production of the microneedle, secondary processing such as laser processing is performed.

As a production method of the microneedle array, the microneedle array can be produced by making, from a microneedle array original plate, a duplication plate in which the projection and recess shape of the microneedle array is reversed; filling minute-pattern portions of the duplication plate thus obtained with polylactic acid which is melted by heating; and cooling down and peeling off the polylactic acid. At this time, the microneedles, which are needles, and the microneedle base for supporting them are molded into an integrated unit. Particularly, in order to obtain noncrystalline microneedles, it is desirable to cool the polylactic acid rapidly at a speed of 30° C./min or more in the cooling step. The duplication plate in which the projection and recess shape of the microneedle array 1 is reversed can be produced by a given method.

Further, the coating agent can contain physiologically active ingredients in purified water and/or a coating carrier, whereby the microneedle and/or the base can be coated with the coating agent, and examples of the coating carrier include polyethylene oxide, hydroxy methylcellulose, hydroxypropyl cellulose, hydroxypropyl methylcellulose, methylcellulose, dextran, polyethylene glycol, polyvinyl alcohol, polyvinyl pyrrolidone, pullulan, carmellose sodium, chondroitin sulfate, hyaluronic acid, dextrin, and gum arabic.

As has been already described above, the height (length) h of the microneedle 3 is preferably 50 μm to 700 μm. Although in the case of the coating of the microneedle 3 the height varies depending on the height h of the microneedle 3, it may be set in a range of 0 μm to 700 μm, usually within a range of 10 μm to 500 μm, preferably about 30 μm to 300 μm. The coating agent applied for coating is fixed by drying after the application.

A liquid composition used for coating the microneedles 3 is prepared by mixing biocompatible carriers, beneficial physiologically active ingredients to be delivered, and in some cases, any of coating aids with a volatile liquid. The volatile liquid can be water, dimethyl sulfoxide, dimethyl formamide, ethanol, isopropyl alcohol, a mixture thereof, and the like. Among them, water is most preferable. A coating agent in a liquid state or a suspension can typically have a concentration of the beneficial physiologically active ingredients of 0.1 to 65% by weight, preferably 1 to 30% by weight, more preferably 3 to 20% by weight. The coating is particularly preferably in a fixed state.

Other known pharmaceutical aids may be added to the coating as long as they do not adversely affect necessary solubility and characteristics of the viscosity of the coating as well as nature and physical properties of the dried coating.

As the physiologically active ingredient (drug) used in the present embodiment, peptide, protein, DNA, RNA, and the like are considered, but no particular limitation is imposed. Examples thereof include α-interferon, β-interferon for multiple sclerosis, erythropoietin, follitropin β, follitropin α, G-CSF, GM-CSF, human chorionic gonadotropin, luteinizing (leutinizing) hormone, salmon calcitonin, glucagon, GNRH antagonist, insulin, human growth hormone, filgrastim, heparin, low molecular weight heparin, and somatropin. Also, examples of a vaccine include Japanese encephalitis vaccine, rotavirus vaccine, Alzheimer's disease vaccine, arteriosclerosis vaccine, cancer vaccine, nicotine vaccine, diphtheria vaccine, tetanus vaccine, pertussis vaccine, Lyme disease vaccine, rabies vaccine, diplococcus pneumoniae vaccine, yellow fever vaccine, cholera vaccine, vaccinia vaccine, tuberculosis vaccine, rubella vaccine, measles vaccine, mumps vaccine, botulism vaccine, herpes vaccine, other DNA vaccines, and hepatitis B vaccine.

An administration method of the microneedle array 1 is not limited in particular, and a device for administration and a supplemental device to fix the microneedle device 1 may be used.

Further, administration time according to the method is not so long, and it is from several seconds to several minutes at longest, and depending on the case, instant administration that takes less than a second is also possible. However, it is also possible to fix the microneedle device 1 on the skin thereafter for continuous administration of active ingredients.

It is to be noted that these drugs may be used solely or two or more thereof may be used in combination. Naturally, any drugs in a form of either an inorganic salt or an organic salt are encompassed as long as the salt is pharmaceutically acceptable. Further, while the drug is basically contained in the coating carrier, it is also possible to prepare a coating carrier without containing the drug, and separately supply the drug afterward via through holes (openings) formed in the microneedle base 5.

EXAMPLES

Example 1

(Production of Microneedle Arrays Having Different Weight-average Molecular Weight)

In Example 1, microneedle arrays of samples 1 to 6 made from respective poly-L-lactic acid resins having different weight-average molecular weights were produced. The respective weight-average molecular weights and microneedle characteristics of the samples 1 to 6 are as shown in Table 1.

(Microneedle Array)
  Height of microneedle: 500 μm
  Shape of microneedle: square pyramid
  Density of microneedle: 625 needles/cm$^2$
  Characteristic: noncrystalline
  Area: 1 cm$^2$ The weight-average molecular weight of each of the samples 1 to 6 was measured by the gel filtration chromatography method (hereinafter referred to as the "GPC method").

(Measurement Conditions)
Column. Shim-pack GPC-803C+GPC-805C (serially-connected)
Column temperature: 45° C.
Eluting solution: Chloroform
Detector: RID (differential refraction detector)
Sample concentration: 2.5 g/L (dissolved in chloroform)
Note that besides the samples 1 to 6, a crystalline microneedle array made from poly-L-lactic acid having a weight-average molecular weight of 40,000 to 100,000 was also produced, but after it was hermetically stored at room temperature for half a year, it was observed that the strength thereof tended to decrease.

TABLE 1

|  | Weight-average molecular weight (Mw) | Molecular weight distribution (Mw/Mn) | Characteristic of microneedle |
|---|---|---|---|
| Sample 1 | 57099 | 1.53 | Noncrystalline (transparent) |
| Sample 2 | 61370 | 1.55 | Noncrystalline (transparent) |
| Sample 3 | 70503 | 1.6 | Noncrystalline (transparent) |
| Sample 4 | 78046 | 1.43 | Noncrystalline (transparent) |
| Sample 5 | 82114 | 1.57 | Noncrystalline (transparent) |
| Sample 6 | 103815 | 1.51 | Noncrystalline (transparent) |

Example 2

In Example 2, a test to measure the strength of microneedles was performed. In the first test, a breaking strength test of a microneedle base was performed in reference to a specification test (K7116) of JIS. The test method was performed as follows: a microneedle base was set up on a special fixture, a load was continually added from an upper side thereof, and time taken before breaking of a test piece and a maximum load at the time of the breaking were measured. The breaking of a microneedle was performed by a special stick attached to an apparatus, and a value of the maximum load which was applied when the microneedle base was broken at its center and a thickness including the needle and the base of the microneedle were taken as a result. As is apparent from results of Table 2, the values of the weight-average molecular weight of the poly-L-lactic acid resin and the maximum load tended to be correlated with each other. From these results, it was demonstrated that the strength of the microneedle is correlated with the weight-average molecular weight.

TABLE 2

|  | Maximum load | Thickness |
|---|---|---|
| Sample 1 | 1284 (g) | 1.20-1.18 (mm) |
| Sample 2 | 1128 (g) | 1.18-1.19 (mm) |
| Sample 3 | 2007 (g) | 1.27-1.31 (mm) |
| Sample 4 | 2305 (g) | 1.24-1.23 (mm) |
| Sample 5 | 2185 (g) | 1.19-1.21 (mm) |
| Sample 6 | 4472 (g) | 1.29-1.30 (mm) |

In the second test, a strength test of a polylactic-acid microneedle was performed with the use of an excised human skin. An excised human skin was adjusted to have a thickness of around 700 μm by an electric dermatome, and fixed on a cork board. Subsequently, a microneedle base was set on the skin and pressed from its back by a finger for 5 seconds at 3 kgf/patch. Microneedles after piercing the skin were subjected to measurement of an outermost-periphery breakage rate using a microscope (Keyence Corporation) so as to measure breakages (breaking, bending) of the needles (Table 3). As for the breakage state of the needles, in all the groups, slight breaking and bending were observed only in microneedles provided at an outermost periphery, but no apparent breaking and bending were observed in needles provided in the second and other rows in any of the groups.

TABLE 3

|  | Microneedle breakage rate (%) except outermost periphery (%) | Outermost-periphery breakage rate (%) |
|---|---|---|
| Sample 1 | 0% | 97% |
| Sample 2 | 0% | 93% |
| Sample 3 | 0% | 96% |
| Sample 4 | 0% | 78% |
| Sample 5 | 0% | 74% |
| Sample 6 | 0% | 89% |

Example 3

Figure 2:
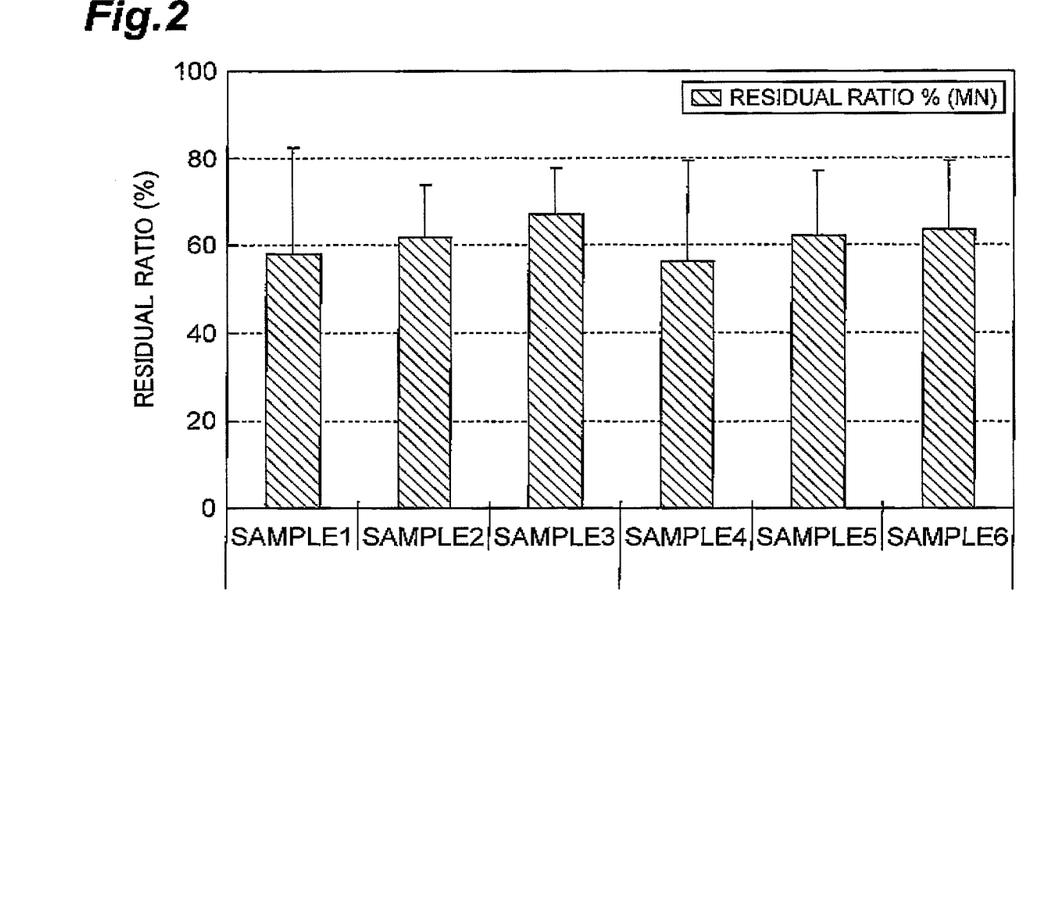
FIG. 2 relates to Example 3 and is a graph showing a result obtained by measuring, by a GM measuring device, a content of a drug remaining on a microneedle base after piercing excised human skin with a coated microneedle device by finger pressing for 5 seconds.

In Example 3, a delivery test (an excised-human-skin piercing test) of a drug was performed with the use of an excised human skin and in the same group configurations as the breaking strength test of the microneedle base. As the drug, radiolabeled $^{14}$C-OVA and Cold OVA were used to prepare a mixed liquid with pullulan. A composition of a coating liquid was assumed (30% pullulan/20% OVA), and coating was performed on tip parts of needles so that the coating had a height of 100 μm. A specific method of the coating was such that coating was performed on a microneedle array by use of a metal mask (standard: one side of an aperture is 220 μm, a thickness is 100 μm, and humidity is 85% or more at room temperature). Subsequently, after piercing an excised human skin with the microneedle device thus coated by finger pressing (3 kg/patch) for 5 seconds, a content of the drug remaining on the microneedle base was measured by a GM measuring device (n=3). As shown in results in FIG. 2, every group shows a residual ratio at the same level, and thus, it was found that the performance of the microneedle was maintained.

Example 4

(Decrease in Weight-average Molecular Weight of Polylactic Acid due to Electron-beam Irradiation)

In Example 4, an experiment was carried out in which samples of respective poly-L-lactic acid resins (weight-average molecular weight: about 15,000 to 140,000) having different weight-average molecular weights were irradiated with an electron beam and decreases in the weight-average molecular weights of the polylactic acids due to the irradiation of the electron beam were measured. Note that the initial weight-average molecular weight of a sample 7 (see FIG. 3) which is a microneedle array is 130,000. Further, the initial weight-average molecular weight of a sample 8 is 90,000. Furthermore, the initial weight-average molecular weight of a sample 9 is 130,000. Moreover, in microneedles of the sample 7, the purity of polylactic acid is 96.5 wt %, and the amount of monomer remaining is 2.1 wt %, and the amount of residual Sn is 99 ppm or less. Further, in microneedles of the samples 8 and 9, the purity of polylactic acid is 96.5 wt %, and the amount of monomer remaining is 0.2 wt %, and the amount of residual Sn is 30 ppm or less.

In this experiment, the weight-average molecular weight of a poly-L-lactic acid resin was measured after microneedles were molded and irradiated with an electron beam of 40 kGy. The measurement of the weight-average molecular weight was performed before molding (in a pellet form), after molding of microneedles, and after electron-beam irradiation, and the weight-average molecular weight at each stage was measured by the gel filtration chromatography method (hereinafter, referred to as the GPC method), similarly to Example 1. Further, as the sterilization method, both an electron-beam sterilization method and a gamma-ray sterilization method were used for comparison, among radiation sterilization methods (see Table 4). Note that Table 4 shows an experimental result on the sample 7.

Figure 3:
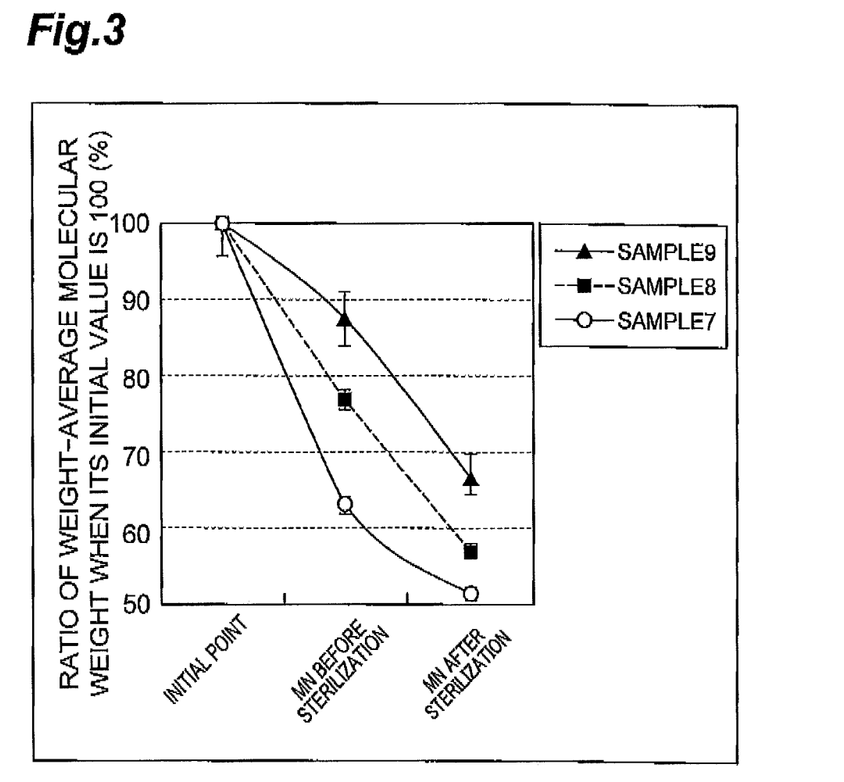
FIG. 3 relates to Example 4 and is a graph showing results obtained by measuring changes in weight-average molecular weight by a gel filtration chromatography method.

As apparent in FIG. 3 and Table 4, it was shown that in the step (heating and cooling) of molding pellet-shape bulk powder into microneedles, the weight-average molecular weight decreased to about 60% to 90% of the weight-average molecular weight before the molding, and the weight-average molecular weight tended to further decrease depending on the irradiation dose by performing radiation sterilization. Moreover, in regard to the electron-beam sterilization method and the gamma-ray sterilization method, when they were compared at the same irradiation dose, it was shown that the electron-beam irradiation method tended to have a lower decreasing rate of the weight-average molecular weight. Note that when the sample 7 and the sample 9 having the same initial weight-average molecular weight were compared with each other, it was shown that the decrease in the weight-average molecular weight tended to be more restrained in the sample 9 having high purity. Measurement conditions and method of the weight-average molecular weight are the same as in Example 1.

Note that the measurement of an electron-beam irradiation dose was performed on the top or bottom of an irradiation sample, or on a supporting material (e.g., a "cardboard"), so as to check that the sample was irradiated with a predetermined irradiation dose (under an irradiation environment with a temperature of 15° C. and a humidity of 15%). On the other hand, in the case of the gamma-ray irradiation, an irradiation sample was irradiated with cobalt-60 gamma rays according to a designated irradiation dose of 5 to 100 kGy, and it was checked by an actual value that it was irradiated at a designated amount.

TABLE 4

| | Irradiation dose (KGy) | Weight-average molecular weight (Mw) | Decreasing rate (%) |
|---|---|---|---|
| Electron-beam irradiation | 0 (Unirradiated) | 73034 | — |
| | 10 | 63181 | 86.5 |
| | 20 | 68165 | 93.3 |
| | 40 | 59382 | 81.3 |
| Gamma-ray irradiation | 0 (Unirradiated) | 77798 | — |
| | 5 | 67777 | 87.1 |
| | 10 | 70657 | 90.8 |
| | 25 | 58221 | 74.8 |
| | 50 | 53046 | 68.2 |
| | 100 | 37747 | 48.5 |

Example 5

In Example 5, in order to evaluate adsorption of a drug (physiologically active ingredients) in a coating composition to a microneedle base, L-polylactic-acid bases (an area: approximately 1 cm$^2$) having a weight-average molecular weight of approximately 80,000 were used, 30 µL of a solution containing a model protein having a weight-average molecular weight of approximately 35,000 and a $^{125}$I label of the model protein was dropped onto the polylactic-acid bases (noncrystalline and crystalline), and the polylactic-acid bases were dried at 40° C. for 1 h and sealed in aluminum packing materials. After the samples were stored at 40° C. for 1 M in a thermostatic chamber, the samples were taken out and the radioactivity thereof was measured by an NAI counter. After that, the samples were immersed in water all night and all day, and the model protein was extracted.

The following day, surfaces of the polylactic-acid bases were washed with water, and the radioactivity which remained on the surfaces of the polylactic-acid bases was measured again by the NAI counter. Note that the evaluation method was performed as follows: a recovery rate was calculated by the following calculation formula and taken as an adsorption index.

Calculation method of the recovery rate: (Counter Value in NAI Apparatus before Extraction−NAI Counter Value after Extraction)/Counter Value in NAI Apparatus before Extraction×100

Drip solution: Twice the amount of pullulan compared to the model protein was added to adjust the solution so that the amount of the drug (the amount of physiologically active ingredients) per base was 30 µg/30 µL.

Figure 4:
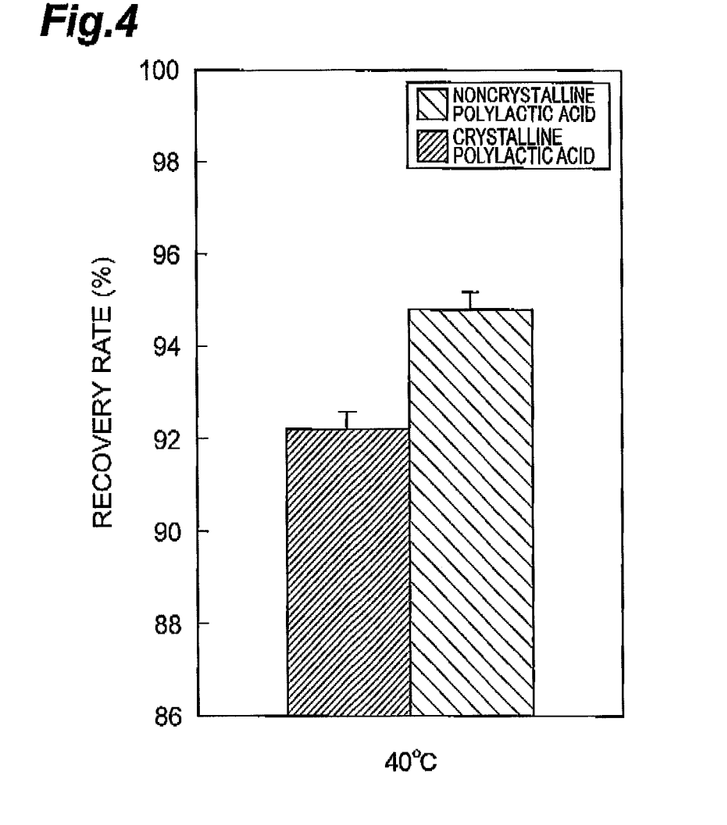
FIG. 4 relates to Example 5 and is a graph showing experimental results to evaluate adsorption of a drug (physiologically active ingredients) in a coating composition to a microneedle base.

As a result thereof, as shown in FIG. 4, the noncrystalline polylactic-acid base is higher in the recovery rate than the crystalline polylactic-acid base, and thus it was found that the adsorption of the drug to the noncrystalline polylactic-acid base is clearly lower than that to the crystalline polylactic-acid base.

Example 6

In Example 6, a noncrystalline microneedle array (a sample 10) and a crystalline microneedle array (a sample 11) each made from poly-L-lactic acid having a weight-average molecular weight of approximately 80,000, were formed. Both of the samples 10 and 11 were arranged as follows: the thickness of a base of the microneedle array was 700 µm, the length of a microneedle was 300 µm, the density of microneedles was 841 needles/cm$^2$, and the area of the microneedle array was 1 cm$^2$. In regard to these samples 10 and 11, a color difference to a color-difference reference color (black) was measured by use of a colorimeter (CR-200, a product made by Minolta Co., Ltd.) by taking a brightness index L* as an index. As a result thereof, the sample 10 showing substantially perfect transparent color had a brightness index L* of 33.7, whereas the sample 11 showing white had a brightness index L* of 60.5. Further, in either of the microneedle arrays of the samples 10 and 11, the purity of polylactic acid is 98.7 wt %, the amount of monomer remaining is 0.5 wt %, and the amount of residual Sn is 50 ppm or less.

Note that the color-difference measurement was performed as follows: after white calibration, measurement was performed by use of a black plate to set a color-difference reference color; and subsequently, a microneedle array was set on the black plate with microneedles turned upward, and measurement was performed thereon.

Further, after the sample 10 and the sample 11 were stored in a desiccator with a humidity of 20 to 30% and a temperature of 24 to 25° C. for approximately 12 months, no deterioration in strength was observed in the sample 10, whereas apparent deterioration in strength was observed in the sample 11, and when force was applied to the sample 11 to bend it, a phenomenon occurred in which the microneedle array was easily broken and damaged. That is, it was checked that the sample 10 was better in storage stability than the sample 11.

Example 7

In Example 7, initially, a silicon base (a microneedle array original plate) of a microneedle-array shape was obtained by precision machining. A duplication plate in which projections and recesses of the silicone base are reversed was set up, and while the duplication plate was heated to heat minute pattern portions of the duplication plate, the minute pattern portions of the duplication plate was filled with heat-melted poly-L-lactic acid (the purity: 99 wt %, the amount of monomer remaining: 0.45 wt %, the amount of residual Sn: 10 ppm or less) having a weight-average molecular weight of approximately 110,000. In a state where the duplication plate was filled with the polylactic acid, the polylactic acid was rapidly cooled down by air-cooling at 80° C. or more per minute, and after the polylactic acid was sufficiently cooled down, it was peeled off from the duplication plate, thereby obtaining a microneedle array made from noncrystalline polylactic acid. Subsequently, in a state where a duplication plate was filled with the polylactic acid, the polylactic acid was rapidly cooled down by air-cooling at 80° C. or more per minute, and the duplication plate was set up on a hot plate warmed to 100° C. After the polylactic acid was heated for a predetermined time, it was rapidly cooled down by air-cooling at 80° C. or more per minute, and peeled off from the duplication plate, thereby obtaining a microneedle array in which the crystallinity of the polylactic acid was changed. The heat time on this hot plate was taken as crystallization processing time.

Approximately 2 mg of the polylactic acid was shaved from the microneedle arrays thus produced, and with the use of a differential scanning calorimeter DSC6200 (SII Nano-Technology Inc.), cut pieces were increased in temperature by 10° C. per minute, and a fusion enthalpy ($\Delta$Hm) and a crystallization enthalpy ($\Delta$Hc) thereof were measured. According to a document, by using the fact that a crystallinity (xc) is given in accordance with xc (%)=100·($\Delta$Hm+$\Delta$Hc)/93 where a fusion enthalpy of 93 J/g, which is of a PLLA crystal with an infinite lamella size is used, the crystallinity of each of the microneedle arrays was calculated. Further, the appearance of the microneedle arrays thus obtained was inspected visually. The criteria for determination are as follows: a microneedle array was put on a black flat plate, and when the whole array was black, it was considered "transparent," when the array was partially white, it was considered "translucent," and when the whole array was white, it was considered "opaque."

Then, with respect to one microneedle in the produced microneedle array, an inspection needle (200 μm in diameter of a test part) was moved to a part of the microneedle which was 100 μm in height from the bottom of the needle, in a parallel direction to the plane of the base at a speed of 0.6 mm per second, and a load applied to the inspection needle and an amount of extension of a needle tip were measured to examine a deformation state of the microneedle. When the inspection needle is pushed into the microneedle and a yield stress or more stress is applied to the microneedle, the microneedle is plastically deformed and the stress decays. A moving distance of the inspection needle from the stage when the yield stress was applied to the microneedle until the stage when the stress decreased to 95% or less of the yield stress was calculated as the amount of extension. At the stage when the stress decreased to 95% or less of the yield stress, a microneedle the needle tip of which was completely separated from the base was considered "broken," and a microneedle the needle tip of which was integrated with the base was considered "bent."

TABLE 5

| Crystallization processing time (min) | Crystallinity (%) | Appearance | Yield stress (gf) | Amount of extension (μm) | Deformation of microneedle |
|---|---|---|---|---|---|
| 0 | 2.3 | Transparent | 110 | 70 | Bent |
| 1 | 5.2 | Transparent | 113 | 65 | Bent |
| 10 | 21 | Translucent | 118 | 40 | Bent |
| 15 | 24 | Translucent | 115 | 38 | Bent |
| 30 | 39 | Opaque | 118 | 0 | Broken |
| 60 | 45 | Opaque | 120 | 0 | Broken |

From the results of Table 5, it was found that when the crystallinity of polylactic acid contained in the microneedle was set to 38% or less, the microneedle array was deformed by bending. Thus, by setting the crystallinity of polylactic acid contained in the microneedle to 38% or less, the microneedle can have an excellent mechanic characteristic. When the crystallinity of polylactic acid contained in the microneedle was set to 25% or less, the needle tip was completely integrated with the base even after it was plastically deformed, and thus the microneedle could have high strength. Note that a relation between the weight-average molecular weight and the strength of the polylactic acid is shown in Table 6.

TABLE 6

| Weight-average molecular weight (Mw) | Molecular weight distribution (Mw/Mn) | Appearance | Yield stress (gf) | Amount of extension (μm) |
|---|---|---|---|---|
| 33000 | 2.75 | Transparent | 62 | 30 |
| 40000 | 1.67 | Transparent | 90 | 65 |
| 55000 | 1.72 | Transparent | 104 | 70 |
| 63000 | 1.50 | Transparent | 112 | 70 |

INDUSTRIAL APPLICABILITY

According to the present invention, it is possible to obtain polylactic-acid microneedle array which maintains functional performance, and the utilization thereof can be markedly increased, and thus the present invention has industrial applicability.

REFERENCE SIGNS LIST

1 ... microneedle array, and 3 ... microneedle.

The invention claimed is:

1. A microneedle array comprising microneedles containing noncrystalline polylactic acid, wherein crystallinity of the polylactic acid is 38% or less and the microneedles are transparent or translucent.

2. The microneedle array according to claim 1, wherein the crystallinity of the polylactic acid is less than 21%.

3. The microneedle array according to claim 1, wherein the crystallinity of the polylactic acid is 2% or more.

4. The microneedle array according to claim 1, wherein the polylactic acid has a weight-average molecular weight of 40,000 to 100,000.

5. The microneedle array according to claim 1, wherein the polylactic acid is poly-L-lactic acid.

6. The microneedle array according to claim 1, wherein the microneedle array is sterilized by electron-beam or gamma-ray irradiation.

7. The microneedle array according to claim 1, wherein the polylactic acid has a purity of 95.0 wt % or more.

8. The microneedle array according to claim 1, wherein the polylactic acid has a purity of 98.7 wt % or more.

9. The microneedle array according to claim 1, wherein the polylactic acid has a purity of 95.0 wt % or more, and has 5 wt % or less of residual monomer and 200 ppm or less of residual Sn.

10. The microneedle array according to claim 1, wherein the polylactic acid has a purity of 98.7 wt % or more, and has 2 wt % or less of residual monomer, and 50 ppm or less of residual Sn.

* * * * *